US006460537B1

(12) United States Patent
Bryant et al.

(10) Patent No.: US 6,460,537 B1
(45) Date of Patent: Oct. 8, 2002

(54) BREATH-ACTUATED AEROSOL DISPENSERS

(75) Inventors: Andrew M. Bryant, Leicestershire; Anthony C. L. Wass, Lincolnshire; Peter D. Hodson, Nottinghamshire, all of (GB)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/437,047

(22) Filed: Nov. 9, 1999

(30) Foreign Application Priority Data

Nov. 16, 1998 (GB) .............................. 9825118

(51) Int. Cl.⁷ ............................................ A61M 11/00
(52) U.S. Cl. .............................. 128/200.23; 128/203.12
(58) Field of Search ...................... 128/200.14, 200.22, 128/200.23, 203.12

(56) References Cited

U.S. PATENT DOCUMENTS

| 3,456,645 A | * | 7/1969 | Brock .................... 128/200.23 |
| 3,456,646 A | | 7/1969 | Phillips et al. .............. 128/173 |
| 3,814,297 A | * | 6/1974 | Warren .................. 128/200.23 |
| 3,826,413 A | * | 7/1974 | Warren .................. 128/200.23 |
| 4,576,157 A | * | 3/1986 | Raghuprasad .......... 128/200.23 |
| 4,664,107 A | | 5/1987 | Wass .................... 128/200.23 |
| 5,027,806 A | * | 7/1991 | Zoltan et al. ........... 128/200.23 |
| 5,069,204 A | * | 12/1991 | Smith et al. ............ 128/200.23 |
| 5,347,998 A | * | 9/1994 | Hodson et al. ......... 128/200.23 |
| 5,408,994 A | * | 4/1995 | Wass et al. ............. 128/200.23 |
| 5,522,378 A | * | 6/1996 | Ritson et al. ........... 128/200.23 |

FOREIGN PATENT DOCUMENTS

| GB | 2292891 A | | 3/1996 | |
| WO | WO 90/13327 | * | 11/1990 | ............. 128/203.12 |
| WO | WO 92/07600 | * | 5/1992 | ............. 128/203.12 |

* cited by examiner

Primary Examiner—Aaron J. Lewis
(74) Attorney, Agent, or Firm—Ted K. Ringared; Robert W. Sprague

(57) ABSTRACT

A dispenser for dispensing a product from a pressurized product container comprising a housing defining a user port and adapted to have a pressurized product container mounted therein, the pressurized product container having a dispensing valve movable relative to the container between an open and a closed position; the housing further comprising a rolling member comprising a vane, and two associated rolling surfaces, the rolling member being capable of rotation in contact with the rolling surfaces such that they translate in opposite directions relative to the rolling member in response to inhalation through the user port, the rolling member being rotatable between a locking position in which the rolling member directly or indirectly engages the pressurized product container or valve to maintain the valve in the closed position, and a release position in which the valve and the pressurized product container move relative to each other so that the valve moves to the open position to dispense product from the container and towards the user port.

13 Claims, 8 Drawing Sheets

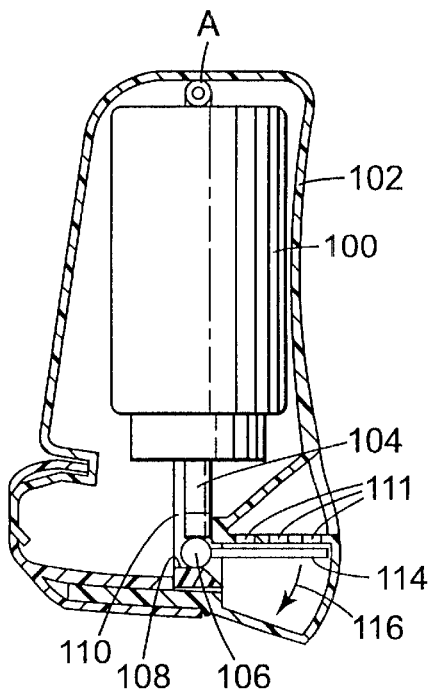
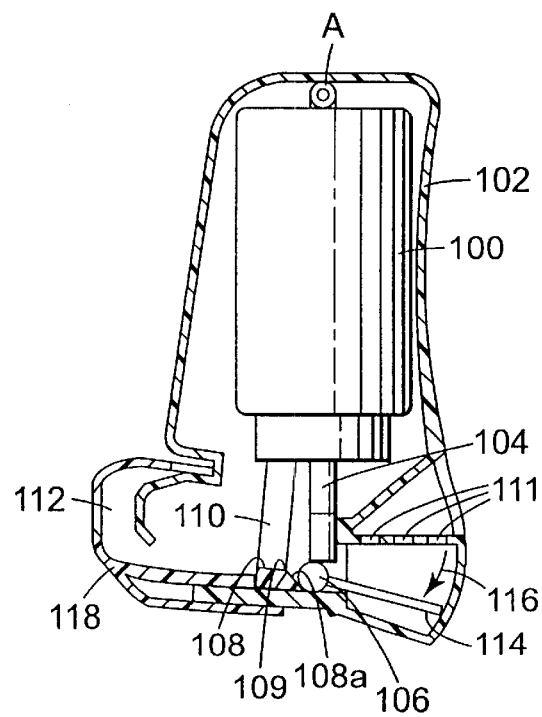
*Fig. 7*  *Fig. 8*
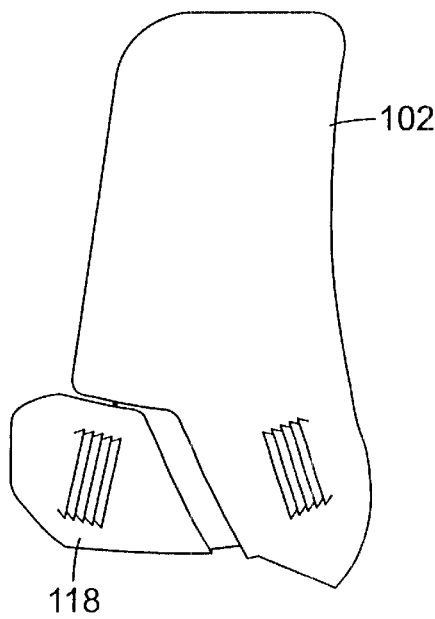
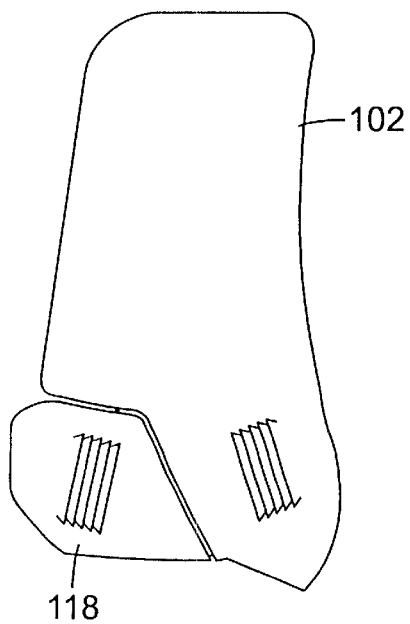
*Fig. 9*  *Fig. 10*

BREATH-ACTUATED AEROSOL DISPENSERS

FIELD OF THE INVENTION

This application claims priority from United Kingdom Serial No. 9825118.4, filed Nov. 16, 1998. This invention relates to a breath-actuated dispenser for administration of a product in the form of aerosolised solid particles or droplets of liquid or suspension or gas. In particular, the invention relates to such devices which are actuated to dispense medicament to a patient in response to the patient's inspiration.

BACKGROUND OF THE INVENTION

It is well known to treat respiratory diseases such as asthma by the inhalation of appropriate medicaments in the form of an aerosol. Conventionally these inhalers use pressurised containers to dispense the medicament in the form of an aerosol through a valve in the container. Various types of valve are known. Firstly, a "press to fire" valve in which a valve stem is pressed to open the valve. Secondly, a "release to fire" valve in which a valve stem is pressed to prime the valve and when the force on the valve stem is released the valve moves to an open position to release the medicament. Other types of valve include a "pull to fire" in which the valve stem is moved outwardly to the firing position and "release to fire on inward stroke" in which the valve stem is held against an inward bias until released to move inwardly and fire. Generally, the valves used are of the "metered dose" type in which when the valve opens only a predetermined, metered dose of the medicament is released from the container.

These known devices are generally manually operated and require a user to manually trigger the inhaler while breathing in. Such devices can be difficult to ensure proper usage since they require coordination often when a patient may be in distress.

Breath-actuated dispensers in which the act of a user breathing in triggers the valve to release the medicament from the container have been proposed in numerous patents. In practice there are few types of breath-actuated dispensers commercially available since it is a complex task to mass produce devices which are capable of meeting the precise requirements of breath-actuator throughout the life of the medicinal aerosol product.

U.S. Pat. No. 3,814,297 discloses a breath-actuated dispenser comprising an aerosol container having a metered dose dispensing valve which is primed by depression and discharges through the stem when the stem is released, a duct having an inlet and outlet, means to receive the aerosol container with the valve stem communicating with the duct, a strut engageable with the stem and manually operable to press the stem inwardly to its priming position, a vane pivotally mounted in the duct movable in response to air flow in the duct and a lever arm attached to the strut and engaged by the pivot whereby when the valve is primed the stem is prevented from moving to its firing position by the strut and when a patent inhales through the outlet the vane pivots causing movement of the lever and strut to release the stem allowing the valve to fire.

GB-2292891 discloses an actuator for a breath-actuated medicament dispenser comprising a cap which is manually depressed to apply a priming/firing force to the dispenser and a restraining means to prevent the device firing until patient inhalation. The restraining means may comprise a piston movable in response to inhalation and a latching device comprising a pivotally mounted latch member whose movement is blocked in the primed position by a ball positioned between the latch member and piston. Movement of the piston in response to inhalation causes the ball to disengage the latch member allowing firing of the device.

SUMMARY OF THE INVENTION

The present invention provides an alternative construction of breath-actuated dispenser. According to the present invention there is provided a dispenser for dispensing a product from a pressurised product container comprising a housing defining a user port and adapted to have a pressurised product container mounted therein, the pressurised product container having a dispensing valve movable relative to the container between an open and a closed position; the housing further comprising a rolling member comprising a vane, and an associated rolling surface, the rolling member being capable of rotation involving relative translational movement along the rolling surface in response to inhalation through the user port between a locking position in which the rolling member is engaged between the rolling surface and the pressurised product container or valve to maintain the valve in the closed position, and a release position in which the valve and the pressurised product container move relative to each other so that the valve moves to the open position to dispense product from the container and towards the user port.

An advantage of the invention is that by providing a rolling member and an associated rolling surface it is possible to provide a breath-actuated dispenser in which the triggering force is reduced compared with the prior art. This is particularly useful when treating patients having respiratory diseases such as asthma. In a situation where the patient requires the inhalation of a medicament, he or she may be unable to inhale strongly and therefore easy triggering of the inhaler is highly advantageous. In addition, it is also possible to provide a breath-actuated dispenser of a relatively simple construction.

In one embodiment the housing comprises a biasing device to apply pressure between the rolling member and the container.

The rolling member comprises a vane which moves in response to air flow generated by inspiration through the user port to cause the rolling member to rotate and translate from the first position to the second position. The vane presents a large surface area to the airflow generated by user inspiration thereby lowering the rate of inhalation required to trigger the device.

In a further embodiment, the pressurised product container is pivotally mounted within the housing and the rolling surface is stationary within the housing. In another embodiment the container is fixed relative to the housing and the rolling surface is pivotally mounted.

It is also preferred that a resetting mechanism be included in the device.

BRIEF DESCRIPTION OF THE DRAWINGS

Embodiments of the invention will now be described by way of example and with reference to the accompanying drawings wherein:

FIG. 7 is a third embodiment according to the invention in a non-firing position;

FIG. 8 is the embodiment of FIG. 7 in a firing position;

FIGS. 9 and 10 are side elevations showing the exterior of the housing of the third embodiment in open and closed positions respectively.

DETAILED DESCRIPTION OF THE ILLUSTRATIVE EMBODIMENTS

Figure 1:
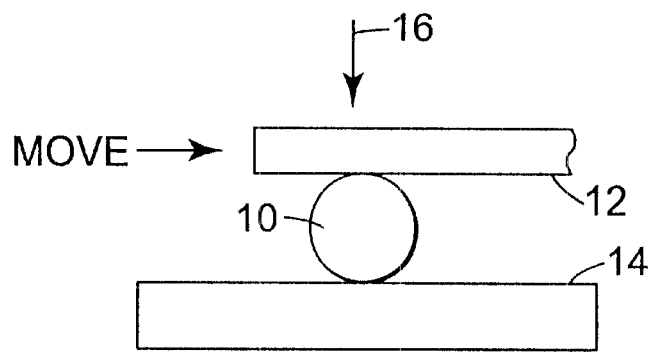
FIG. 1 illustrates the principle of the invention.

FIG. 1 shows in diagrammatic form a rolling member 10 held between two surfaces 12, 14. Arrow 16 represents a downward force on the surface 12. When either surface is moved relative the other, in a direction transverse to force 16, the rolling member 10 will remain in contact with both surfaces 12, 14. Since there is no sliding movement between the rolling member 10, and either of the two surfaces 12, 14, the relative movement between the upper 12 and lower 14 surfaces is essentially frictionless. The force required to move the surfaces 12, 14 relative each other in such a manner is therefore minimal despite the presence of the downward force 16.

This principle can be utilised to reduce the forces required in a triggering mechanism for use of a breath-actuated inhaler. In accordance with the invention the rolling member comprises a vane which is positioned to move in response to inhalation.

Figure 2:
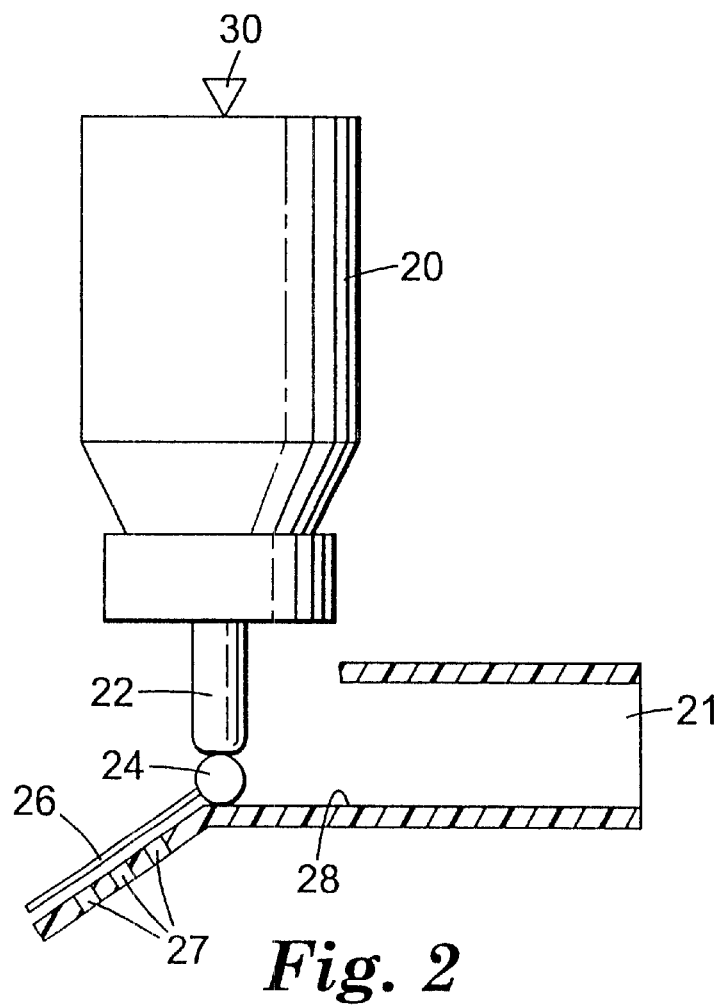
FIG. 2 shows an embodiment of the invention in which the rolling member is powered by the user's inhalatory effort.

The first embodiment, shown in FIG. 2 uses a pressurised container 20 having a "release to fire" valve comprising a valve stem 22. In the non-firing position illustrated in FIG. 2, a rolling member 24 having a vane 26 is disposed between a rolling surface 28 and the valve stem 22. In this position the valve stem 22 is pressed towards the container 20, compressing the spring within the valve and thereby preventing the release of the metered dose of product. It is preferred that the container 20 be pivotally mounted within a housing (not shown) at point 30 on the container's base. The method of pivoting is preferably one which minimizes frictional effects.

Figure 3:
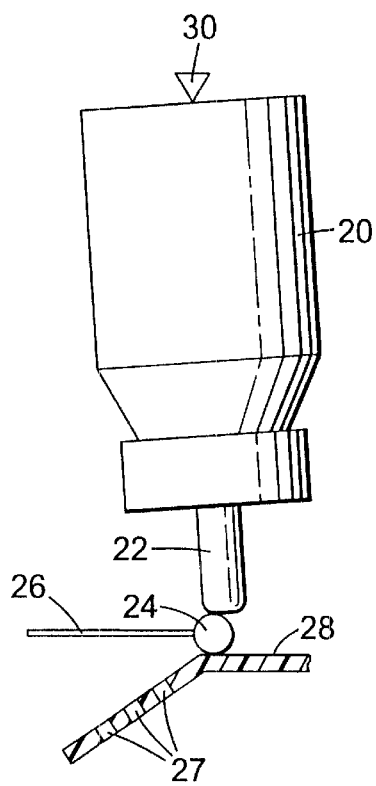
FIG. 3 is the device shown in FIG. 2 during triggering.
Figure 4:
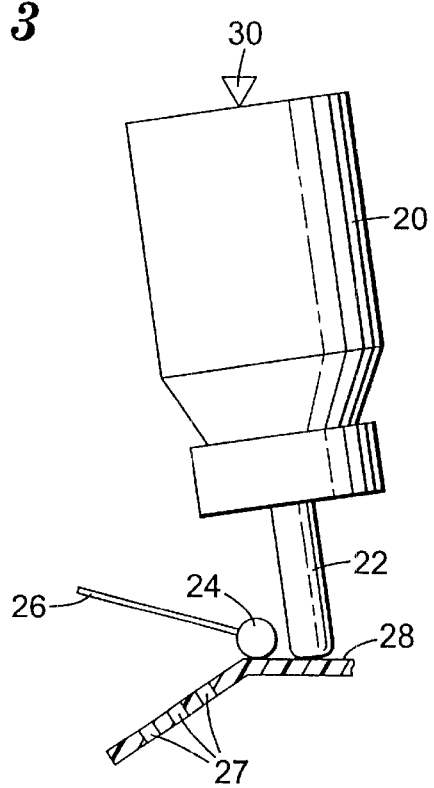
FIG. 4 is the device shown in FIG. 2 in its triggered position.

In order to activate the device a user inhales through a mouthpiece 21, schematically represented in FIG. 2. This will result in a pressure drop being created within the housing (not shown) thereby generating a pressure difference across the vane 26. As a result air is drawn into the housing via holes 27 causing the vane to pivot about the rolling member which rotates the rolling member 24 along the rolling surface 28 as shown in FIG. 3. The rotation of the rolling member causes the valve stem 22 to pivot towards the mouthpiece 21 on the rolling member 24 until the valve stem 22 drops off the rolling member as illustrated in FIG. 4. In this position the spring within the valve is allowed to extend thus pushing the valve stem 22 away from the container 20 to fire thereby releasing the metered dose of product.

In this embodiment, the rolling surface may either remain stationary relative the housing whilst the container and valve stem moves during triggering or vice versa.

Figure 5:
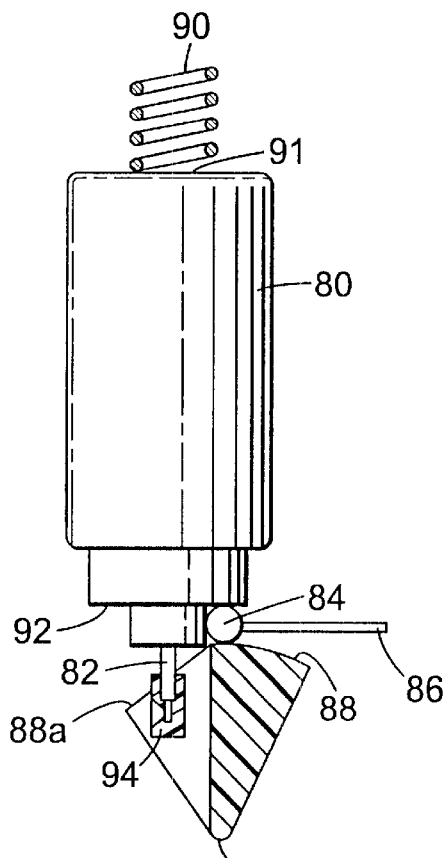
FIG. 5 shows a second embodiment according to the invention in its non-firing position.
Figure 6:
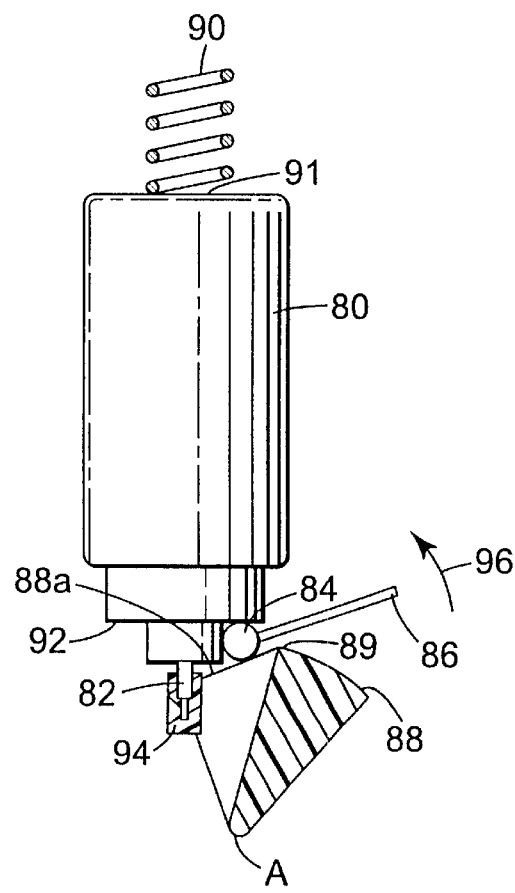
FIG. 6 is the embodiment shown in FIG. 5 in its firing position.
Figure 11:
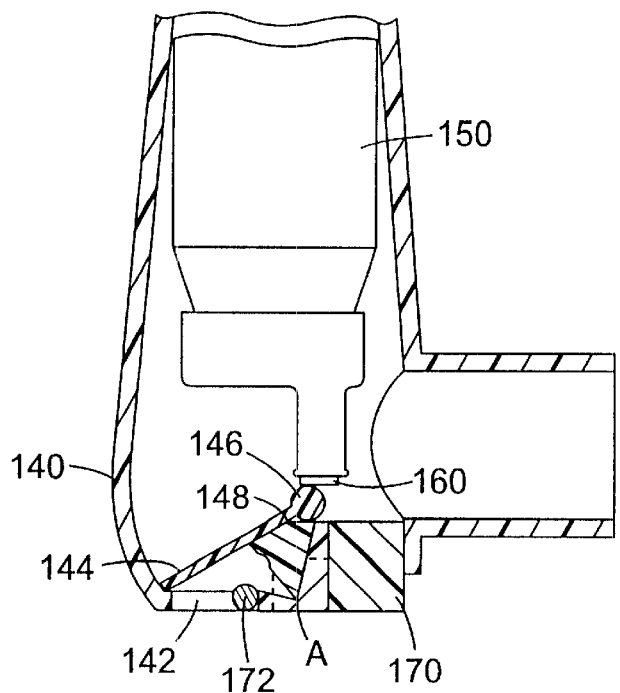
FIG. 11 is a diagram of a fourth embodiment according to the invention in a primed position.

FIGS. 5 and 6 represent a second embodiment of the invention in a non-firing and firing position respectively. In FIG. 6 a pressurised container 80, having a "press to fire" valve comprising a valve stem 82 held within a housing (not shown). A rolling member 84 having a vane 86 is disposed between a rolling surface 88, 88a and the container 80. The rolling surface 88, 88a is pivotally mounted about A. A spring 90 disposed between the base 91 of the container 80 and the housing (not shown) urges a shoulder 92 of the container 80 into contact with the rolling member 84 and consequently urges the rolling member 84 into contact with the rolling surface 88. The valve stem 82 fits tightly into a stem socket 94 which incorporates a spray exit nozzle. The stem socket 94 remains static relative to the housing throughout the entire triggering cycle of the pressurised container 80.

Upon inhalation by the user, an airflow is generated in a manner similar to that described with reference to FIGS. 2 to 4, which acts to impel the vane 86 in a direction indicated by arrow 96 as shown in FIG. 6. Since the container 80 is prevented from moving in a horizontal direction, the rolling surface 88 is caused to move as the rolling member 84 rotates. The rolling surface 88, 88a pivots (clockwise as shown in FIG. 6) about point A.

The rolling surface is configured to provide a stable non-firing region 88 which is preferably a cylindrical surface having an axis at point A and an unstable firing region 88a where the rolling surface is closer to point A than the stable region 88. A triggering region 89 is located between the stable and non-stable regions.

Movement of the vane 86 in direction 96 in response to inhalation results in the rotation of the rolling member 84 which in turn results in the rolling surface pivoting about point A. The rolling surface pivots in a clockwise direction from its non-firing position shown in FIG. 5, to a firing position shown in FIG. 6. As the surface pivots clockwise, the distance between the surface 88 and point A decreases. As the rolling surface pivots clockwise, initially the rolling member 84 will remain in contact with the stable region 88 of the rolling surface and the valve stem will remain in the non-firing position. Further pivoting causes the valve stem to pass through the triggering region 89 to the unstable firing region 88a of the rolling surface. In this region the distance between the rolling surface 88a and the pivot point A decrease and as a result, the container 80 is caused to move downwards under the influence of the spring 90. Thus, the valve stem is pressed into the container resulting in the release of the metered dose of product. The system can be reset by rotating the rolling surface in an anti-clockwise direction back to the non-firing position illustrated in FIG. 5.

A third embodiment of the invention is shown in FIGS. 7 and 8 again in a non-firing and a firing position respectively. The canister 100 is equipped with a "release to fire" valve and is held stationary within the housing 102 at all times. When in a non-firing position as shown in FIG. 7, the valve stem 104 is prevented from extending and firing by rolling member 106 and rolling surface 108. The rolling surface is pivotally connected to point A via a shaft 110. Within the valve of the container 100, there is a valve spring which urges the valve stem 104 into contact with the rolling member 106 which in turn urges the rolling member 106 into contact with the rolling surface 108.

The rolling surface comprises a stable non-firing region 108 and an unstable firing region 108a separated by a triggering region 109 in a similar manner to the embodiment of FIGS. 5 and 6. However, since the pivot point A is located in a different position in this embodiment, the unstable region 108a of the rolling surface increases in distance from the pivot point A compared to the stable region 108.

To release the product from the pressurised container 100, a user inhales through user port 112 which creates a pressure drop within the housing. In order to equalise the pressure difference between the inside and the outside of the housing 102, air flows into the housing 102 via holes 111. This airflow acts upon vane 114 impelling it to move in a direction indicated by arrow 116. This results in rotation of the rolling member 106, causing the rolling surface 108 to pivot clockwise from the non-firing position shown in FIG. 7 to the firing position shown in FIG. 8. As the rolling surface pivots the rolling member passes through the triggering region 109 to the unstable firing region 108a of the rolling surface. As the distance between the pivot point A and rolling surface 108a increases so does the distance between the stationary container and rolling surface 108a. This increase in distance resulting from the movement allows the valve stem to extend under the influence of the valve spring and hence firing the valve to release a spray of medicament. This mechanism can be reset by pushing rolling surface 108 back to the non-firing position shown in FIG. 7. This is achieved by moving a cap 118 over the user port 112 as shown in FIGS. 8 and 9 and then pushing the cap 118 to a closed position as shown in FIGS. 7 and 10. This causes the cap 118 to press directly against the rolling surface 108 thereby resetting the triggering mechanism and locking it until the cap 118 is removed.

Figure 12:
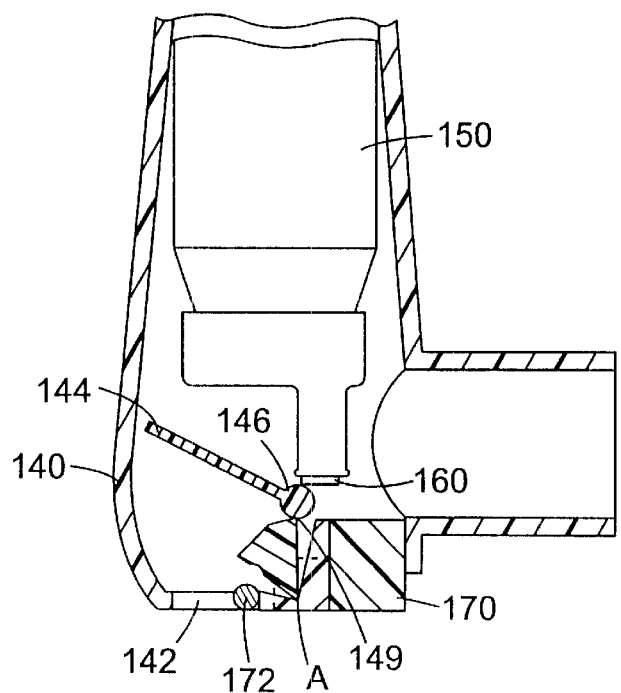
FIG. 12 shows the embodiment of FIG. 11 during the triggering process.
Figure 13:
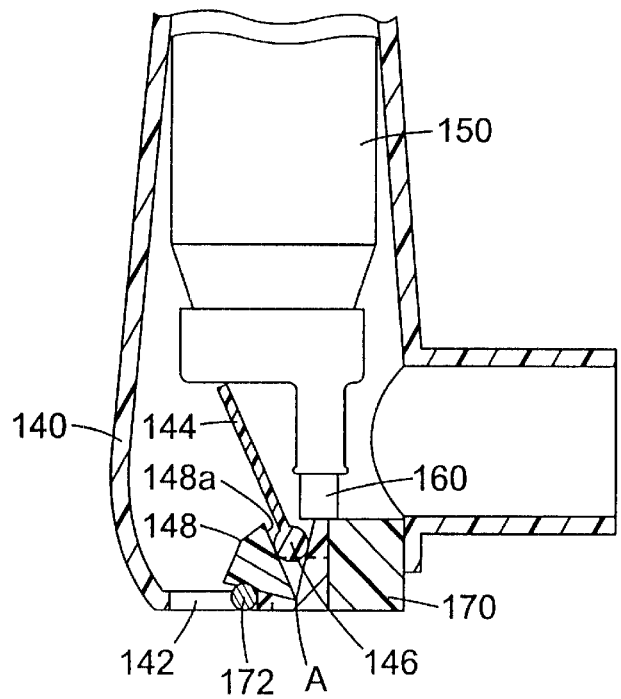
FIG. 13 shows the embodiment of FIG. 11 in a firing position.
Figure 14:
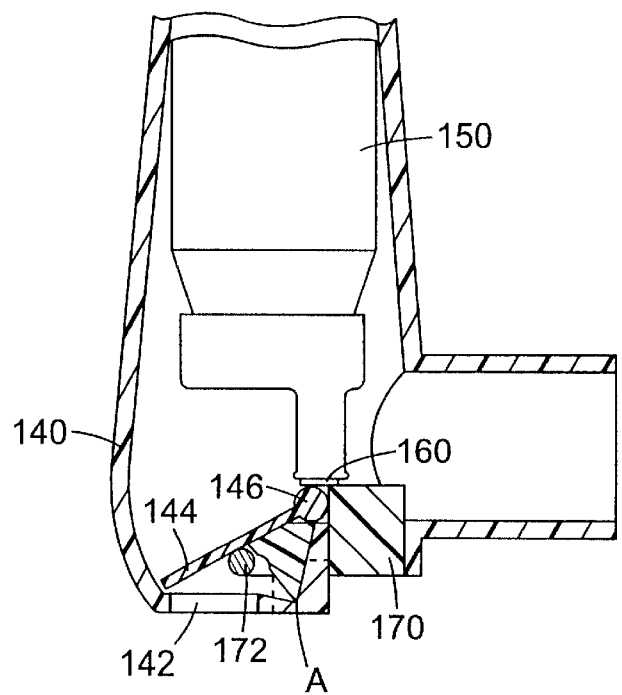
FIG. 14 shows the embodiment of FIG. 11 being reset.

The fourth embodiment of the invention illustrated in FIGS. 11 to 14 works in a similar manner to the third embodiment shown in FIGS. 7 to 10. Again, the pressurised container in this embodiment is equipped with a "release to fire" valve and the rolling member is located between the rolling surface and the valve stem when in the non-firing position, thus preventing the release of product. Similarly, when the user inhales through the user port, a partial vacuum is created inside the housing 140, thus creating a pressure difference between the inside and outside of the housing 140. This results in air flowing in through hole 142 which acts on vane 144 causing the rolling member to roll clockwise resulting in the rolling surface 148 pivoting anti-clockwise about point A as shown in FIG. 12.

The rolling surface has a stable region 148, a triggering region 149 and a non-stable firing region 148a. When the rolling surface pivots to the position illustrated in FIG. 13, the rolling member passes through the triggering region 149 and drops into a wedged shape gap formed by the unstable region 148a of the rolling surface allowing the valve stem 160 to move under the influence of the valve spring thereby releasing the product.

In order to reset the inhaler according to this fifth embodiment of the invention, reset button 170 is urged upwards causing the valve stem 160 to move towards the container 150 to its non-firing position. Rod 172 is connected to reset button 170 such that when reset button 170 is pressed upwards, rod 172 impels the rolling surface to pivot back to its non-firing position shown in FIG. 14 thereby forcing the rolling member upwards to the primed position shown in FIG. 11. The reset button 170 and rod 172 may be used to lock the device to prevent accidental actuation when not in use.

FIGS. 15 to 18 represent diagrams of a further embodiment in accordance with the invention showing the devices in the primed position, during inhalation, during firing and during resetting respectively. The improvement illustrated in these Figures is similar to that illustrated in FIGS. 5 and 6, and like references refer to like parts.

The embodiment of FIGS. 15 to 18 differs from that of FIGS. 5 and 6 in that the device additionally comprises a lever 200 which is pivoted about point 202 and has a lower surface 204 in contact with the rolling member 84 and an upper surface 206 which contacts the aerosol container 80 or a valve ferrule attached thereto.

Figure 15:
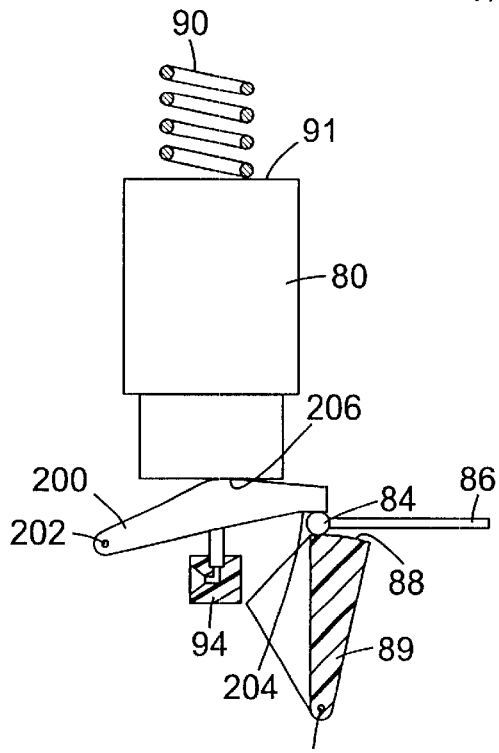
FIGS. 15 to 18 are diagrams of a further embodiment of the invention in the primed position, during initial inhalation, during firing and during resetting, respectively.

In the primed position as shown in FIG. 15, movement of the aerosol container to fire the valve is impeded by lever 200. Lever 200 is maintained in a static position by rolling member 84 and associated rolling surface 88 provided on rolling surface member 89.

Figure 16:
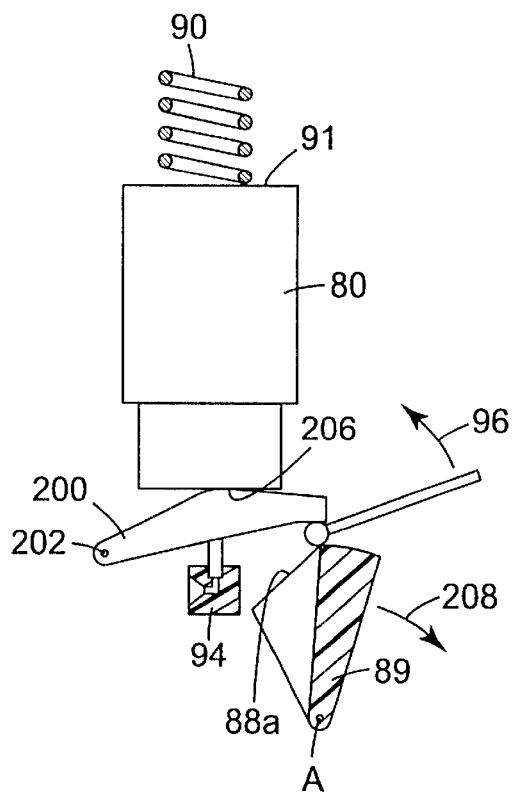
Figure 17:
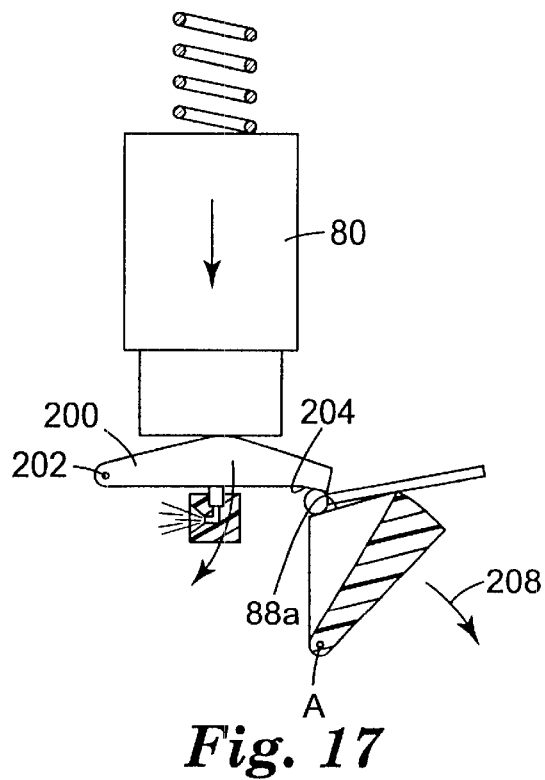

Upon inhalation by the user, an airflow is generated which acts to impel vane 86 in the direction indicated by the arrow 96 in FIG. 16. Movement of the vane 86 causes the rolling member 84 to rotate. The lever 200 is prevented from moving in a horizontal direction and rotation of the rolling member 84 causes the rolling surface 88 to move resulting in rolling surface member 89 pivoting about point A in the direction of the arrow 208.

Further movement of the vane causes the rolling member 84 to come into contact with the unstable firing region 88a of the rolling surface. In this region there is downward movement of the rolling member 84 and associated end of the lever 200 thereby allowing downward movement of the aerosol container 80 under the influence of the spring 90 (FIG. 17) causing firing of the valve.

Figure 18:
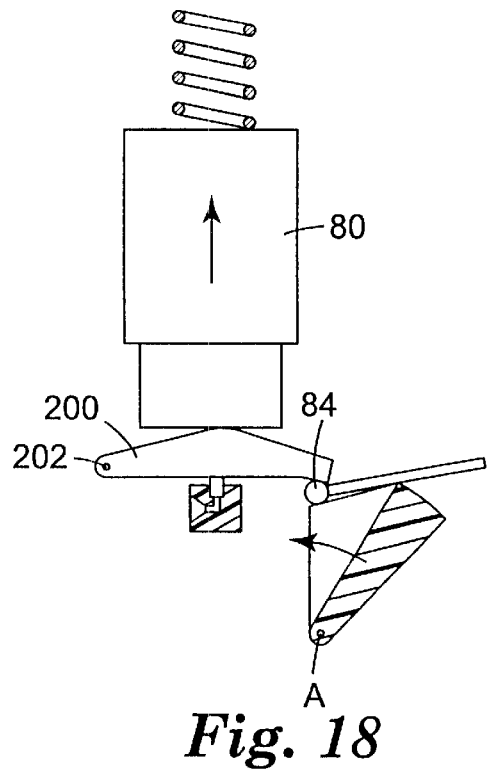

The device is reset by rotating the rolling surface member 89 in an anti-clockwise direction as illustrated in FIG. 18. This causes associated movement of the rolling member 84 and lever 200 which pivots about point 202 resulting in upward movement of the aerosol container 80 to the primed position shown in FIG. 15.

The presence of the lever assists in reducing the force required to reset the device. Also, it is easy to fabricate a lever having a smooth surface 204 in contact with the rolling member. It is not always practical to provide a flat surface on a valve ferrule (as shown in FIGS. 5 and 6) since the ferrule is often crimped to hold components of the valve in place and is crimped around the aerosol container which may result in imperfections on the surface intended to contact the rolling member (84).

It will be appreciated that FIGS. 2 to 18 are of a diagrammatic nature and disclose only the essential components for appreciating the concept of the invention. For example, the device will incorporate moulding or other means to prevent the rolling member and associated vane from becoming dislodged from its functioning positions. An end stop may be provided to prevent excessive movement of the vane and the member forming the rolling surface may be provided with pins positioned in slots on either side of the rolling member.

What is claimed is:

1. A dispenser for dispensing a product from a pressurised product container comprising a housing defining a user port and adapted to have a pressurised product container mounted therein, the pressurised product container having a dispensing valve movable relative to the container between an open and a closed position; the housing further comprising:

a rolling member comprising a vane connected to the rolling member, and an associated rolling surface in contact with the rolling member, the rolling member being capable of rotation in contact with the rolling surface such that the rolling member translates in the opposite direction relative to the rolling surface in response to inhalation through the user port, the rolling member being rotatable between a locking position in which the rolling member directly or indirectly engages the pressurised product container or valve to maintain the valve in the closed position, and a released position in which the valve and the pressurised product container move relative to each other so that the valve moves to the open position to dispense product from the container and towards the user.

2. A dispenser as claimed in claim 1 wherein the housing further comprises a spring to apply pressure between the rolling member and the container.

3. A dispenser as claimed in claim 1 wherein the vane limits movement of the rolling member.

4. A dispenser as claimed in claim 1 wherein the rolling member is at least partially circular in cross-section.

5. A dispenser as claimed in claim 1 wherein the shape of at least one of the rolling surfaces is designed to provide a desired resistance to the rotation of the rolling member.

6. A dispenser as claimed in claim 1 wherein the pressurised product container is pivotally mounted within the housing.

7. A dispenser as claimed in claim 6 in which in its locking position the rolling member engages and blocks movement of the valve stem and disengages the valve stem when moved to its release position to allow firing of the valve.

8. A dispenser as claimed in claim 1 wherein a rolling surface is pivotally mounted within the housing.

9. A dispenser as claimed in claim 8 in which a rolling surface comprises a stable non-firing region which engages the rolling member in its locking position and an unstable firing region, whereby movement of the rolling member towards its release position causes pivoting of the rolling surface such that the unstable firing region engages the rolling member.

10. A dispenser as claimed in claim 9 which additionally comprises a blocking lever having an upper surface contacting the pressurised product container and a lower surface in contact with the following surface whereby movement of the rolling member to its release position causes pivoting of the blocking lever to allow movement of the pressurised product container to fire the valve.

11. A dispenser as claimed in claim 1 wherein the valve of the pressurised product container is of a press to fire configuration.

12. A dispenser as claimed in claim 1 wherein the valve of the pressurised product container is of a release to fire configuration.

13. A dispenser as claimed in claim 1 further comprising a resetting mechanism.

* * * * *